United States Patent [19]

Young et al.

[11] Patent Number: 5,017,583
[45] Date of Patent: May 21, 1991

[54] LEUKOTRIENE ANTAGONISTS

[75] Inventors: Robert N. Young, Senneville; Joshua Rokach, Chomedy; Haydn R. Williams, Dollard Des Ormeaux; Masatoshi Kakushima, Quebec; Yvan Guindon, Ile Bizard, all of Canada

[73] Assignee: Merck Frosst Canada, Inc., Kirkland, Canada

[21] Appl. No.: 159,631

[22] Filed: Feb. 23, 1988

Related U.S. Application Data

[60] Continuation of Ser. No. 861,942, May 12, 1986, abandoned, which is a division of Ser. No. 591,343, Mar. 19, 1984, Pat. No. 4,609,744, which is a continuation-in-part of Ser. No. 487,331, Apr. 21, 1983, abandoned.

[51] Int. Cl.$^5$ ............... A61K 31/47; C07D 215/227; C07D 215/54; C07D 215/56
[52] U.S. Cl. ................... 514/312; 514/311; 514/313; 514/314; 544/336; 544/405; 544/408; 544/409; 548/252; 548/469; 548/494; 548/495; 548/503; 548/517; 548/518; 548/528; 548/541; 548/543; 549/402; 549/416; 549/417; 549/420; 549/214; 549/423; 549/468; 549/561; 560/9; 560/10; 560/15; 560/16; 560/17; 560/18; 560/22; 560/53; 560/55; 560/60; 562/426; 562/427; 562/431; 562/581; 564/440; 568/813; 570/182; 570/185; 546/153; 546/154; 546/155; 546/156; 546/157; 546/159; 546/162; 546/168; 546/169; 546/170; 546/172; 546/173; 546/174; 546/175; 546/176; 546/178; 546/268; 546/329; 546/330; 546/339; 546/340; 546/341; 546/342
[58] Field of Search ............... 546/156, 157, 153, 154, 546/155, 173, 174, 175, 168, 169, 170, 159, 162, 172, 178, 176; 514/311, 312, 314, 313

[56] References Cited

U.S. PATENT DOCUMENTS

| | | | |
|---|---|---|---|
| 3,351,525 | 11/1967 | Hodel | 546/178 |
| 4,156,726 | 5/1979 | Brown et al. | 514/284 |
| 4,289,777 | 9/1981 | Albrecht et al. | 546/156 |
| 4,296,129 | 10/1981 | Kadis | 424/309 |
| 4,444,584 | 4/1984 | Serban et al. | 71/94 |
| 4,609,744 | 9/1986 | Young et al. | 546/157 |
| 4,631,287 | 12/1986 | Chakraborty et al. | 514/307 |
| 4,745,127 | 5/1988 | Atkinson et al. | 514/469 |
| 4,749,406 | 6/1988 | Martin | 546/178 |
| 4,749,699 | 6/1988 | Atkinson et al. | 514/224.5 |
| 4,761,425 | 8/1988 | Girard et al. | 514/456 |
| 4,785,004 | 11/1988 | Von Sprecher et al. | 514/311 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |

FOREIGN PATENT DOCUMENTS

| | | |
|---|---|---|
| 0068739 | 1/1983 | European Pat. Off. . |
| 57-118555 | 7/1982 | Japan . |
| 1042638 | 9/1966 | United Kingdom ............... 546/157 |
| 2058785 | 4/1981 | United Kingdom . |
| 2094301 | 9/1982 | United Kingdom . |

OTHER PUBLICATIONS

"The Merck Index", (10th Ed.), p. 2582 (entry #2580) (1983).
Goldenberg, Chemical Abstracts, vol. 105, No. 60305z, (1986).
Piper et al., Ann Rpts. Med. Chem., 15 69 (1980).
Borgeat and Sirois, J. Med. Chem., 24 121 (1981).
Samuelsson, Science, 220 568 (1983).
Bailey et al., Ann Rpts. Med. Chem. 17 203 (1982).

Primary Examiner—Mukund J. Shah
Assistant Examiner—E. Bernhardt
Attorney, Agent, or Firm—Gabriel Lopez; Joseph F. DiPrima

[57] ABSTRACT

Compounds of the Formula I:

$$A-(\underset{\underset{R^2}{|}}{\overset{\overset{R^2}{|}}{C}})_c-(CH\underset{n}{-}CH_n)_a-\underset{\underset{B-X}{|}}{\overset{\overset{R^2}{|}}{C}}-CH_n-(\underset{\underset{R^3}{|}}{\overset{}{CH}}\underset{n}{-}CH_n)_b-(\underset{\underset{R^2}{|}}{\overset{\overset{R^2}{|}}{C}})_c-R^1 \quad I$$

and pharmaceutically acceptable salts thereof are leukotriene antagonists. These compounds inhibit SRS-A and leukotriene synthesis and are antagonists of SRS-A and are thus useful in the treatment of asthma, allergic disorders, inflammation, skin diseases and certain cardiovascular disorders.

2 Claims, No Drawings

LEUKOTRIENE ANTAGONISTS

REFERENCE TO RELATED APPLICATION

This is a continuation of application Ser. No. 861,942, filed May 12, 1986, now abandoned, which is a division of U.S. Ser. No. 591,343, filed Mar. 19, 1984, now U.S. Pat. No. 4,609,744, which is a continuation in part of U.S. Ser. No. 487,331, filed Apr. 21, 1983, now abandoned.

BACKGROUND OF THE INVENTION

This invention is directed to new chemical compounds, especially useful as antagonists of the slow reacting substance of analphylaxis (SRS-A) and the major components thereof, the leukotrienes $C_4$, $D_4$ and $E_4$; as well as of leukotriene $B_4$.

It is known that certain substances play an important role in inducing an allergic reaction, such as asthma, allergic bronchitis or allergic rhinitis, in man. Examples of such substances are SRS-A and its major components, the leukotrienes. See: P. Borgeat and P. Sirois, *J. Med. Chem.*, 24, 121 (1982) and P. J. Piper, *Ann. Rpts. Med. Chem.*, 15 69 (1980).

SRS-A and the leukotrienes $C_4$, $D_4$ and $E_4$, affect the smaller peripheral airways of the larger central passages such as the trachea and the bronchi. In the presence of an allergic trigger like pollen or dust, these leukotrienes are manufactured from fatty substances trapped in the membrane of a triggered cell. A series of reactions within the cell generates this mixture of leukotrienes which may then pass through the cell membrane into the bloodstream. Once in the blood, these leukotrienes constrict air passages producing breathlessness.

Leukotriene $B_4$, which is not part of SRS-A, is an important chemotactic factor which induces migration of polymorphic cells and thus contributes to both inflammation and allergic diseases.

SUMMARY OF THE INVENTION

This invention is directed to novel compounds of the Formula I:

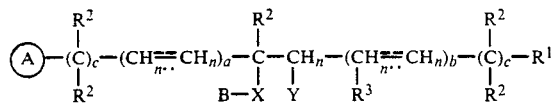

and pharmaceutically acceptable salts thereof wherein the various substituents are as defined herein below.

This invention provides compounds that act as antagonists to prevent or reverse the actions of leukotrienes $C_4$, $D_4$ and $E_4$, and SRS-A and also leukotriene $B_4$.

This invention also provides a method to prevent the synthesis and/or release of SRS-A or the leukotrienes $C_4$, $D_4$ and $E_4$ as well as leukotriene $B_4$, in a human subject. This method comprises administering to said subject an effective amount of a compound of Formula I or a pharmaceutically acceptable salt thereof, optionally in a pharmaceutically acceptable carrier.

Finally, methods of preparing the compounds of Formula I are provided herein.

DETAILED DESCRIPTION OF THE INVENTION

The present invention is directed to novel compounds which have activity as antagonists of SRS-A and leukotrienes. The invention is also directed to methods of preparation and to methods of using the novel compounds described herein. Because of their activity as leukotriene antagonists, the compounds of the present invention are useful in preventing and treating allergic conditions such as, chronic bronchitis, allergic rhinitis, asthma; skin diseases such as, psoriasis, atopic exema; inflamation and cardiovascular disorders such as angina.

The compounds of this invention are best realized by Formula I:

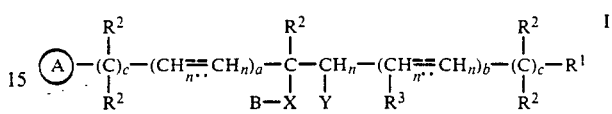

and pharmaceutically acceptable salts thereof, wherein;
  X is O, S, SO, $SO_2$;
  n is 0-2 as required to maintain four bonds to carbon;
  the broken lines represent optional double and triple bonds;
  b and c are each independently 0 to 5;
  $R^1$ is $COOR^2$, $CH_2OH$, CHO, tetrazole, hydroxymethyl ketone, CN, $CONR^2R^4$, a monocyclic or bicyclic heterocyclic ring containing an acidic hydroxyl group or $NHSO_2R^4$; or

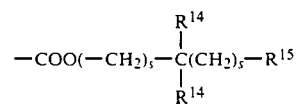

wherein each s is independently 0-3; each $R^{14}$ is independently H or alkyl of 1 to 4 carbons which may be straight chain or branched; $R^{15}$ is
  (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
  (B) the radical $X-R^{16}$ wherein X is O, S or NH and $R^{16}$ contains up to 21 carbon atoms which may be straight chain or branched and is (1) a hydrocarbon radical or (2) an acyl radical of an organic acyclic or monocyclic carboxylic acid containing not more than 1 heteroatom selected from N, O or S in the ring;
  $R^2$ and $R^3$ are each independently H, lower alkyl or one $R^2$ and one $R^3$ may be connected by a 1C or 2C containing bridge to form a cyclic ring which may have 0, 1, 2 or 3 double bonds;
  $R^4$ is H; alkyl; hydroxyl; halogen; haloalkyl; benzyl; benzyl substituted with at least one $R^7$; aryl; alkylarylalkyl; aryl substituted with at least one $R^5$; $NO_2$; CN; $SCF_3$; $OR^5$; O-benzyl; O-benzyl substituted with at least one $R^5$; O-aryl; O-aryl substituted with at least one $R^5$; $SR^5$; $NR^2R^5$; $SOR^5$ or $SO_2R^5$;
  $R^5$ is H; alkyl; hydroxyl; halogen; haloalkyl; alkylarylalkyl; benzyl; benzyl substituted with at least one $R^3$; $NO_2$; CN; $SCF_3$; $OR^3$; O-benzyl; O-benzyl substituted with at least one $R^3$; O-aryl; O-aryl substituted with at least one $R^3$; $SR^3$; $NR^2R^3$; $SOR^3$ or $SO_2R^3$;
  Y is H, OH, $OR^2$ or $=O$;
  (A) is H,

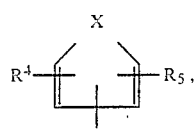
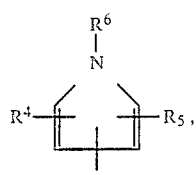
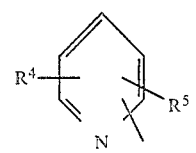
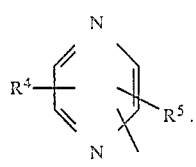
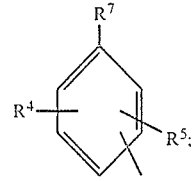
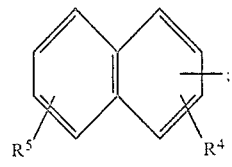
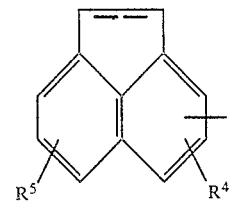
wherein the broken line represents an optional double bond;
R⁶ is H, lower alkyl, halogen, OR² or SR²;
R⁷ is H, alkylthioalkyl, alkylthiobenzyl or alkylthioaryl;
B is H,
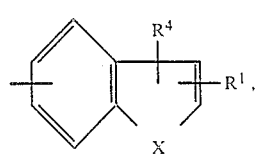
-continued
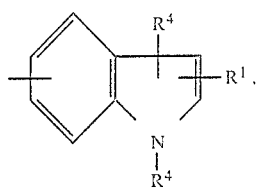
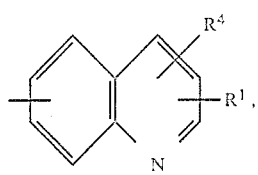
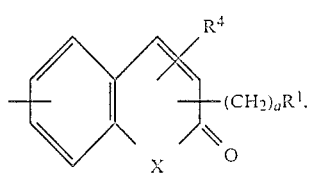
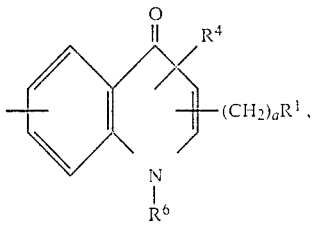
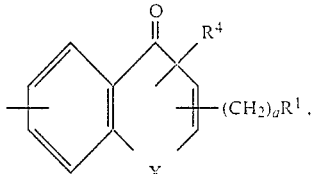
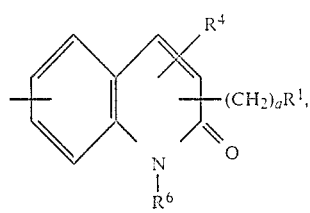
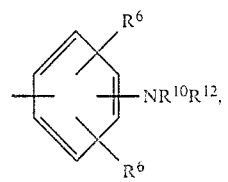
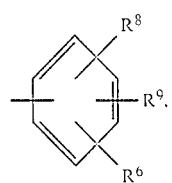

-continued

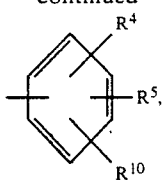

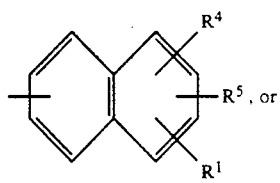

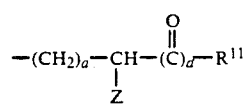

wherein
Z is H, NHR$^9$, NR$^2$R$^9$, an N-terminal bonded essential amino acid or a lower alkyl ester thereof, OH, OR$^4$ or OR$^2$;
R$^8$ is H, lower alkyl or —(CH$_2$)$_a$R$^1$;
R$^9$ is H,

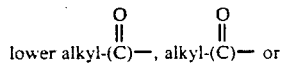

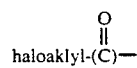

R$^{10}$ is

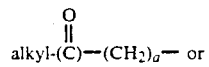

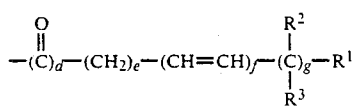

wherein e is 0 to 9 and f and g are independently 0 to 3;
R$^{11}$ is Z, wherein Z is as defined above, when d is 1, and R$^{11}$ is R$^1$ or Z, wherein Z is as defined above, when d is 0;
R$^{12}$ is H, acyl, formyl, CN or SO$_2$R$^{13}$;
R$^{13}$ is H, alkyl or aryl;
each a in the above definitions is independently 0 to 5 and each d in the above definitions is independently 0 or 1.

As used herein, the term "lower alkyl" means those alkyl groups of from 1 to 7 carbon atoms of either a straight, branched or cyclic configuration. The term also means carbon fragments having one or more double or triple bonds. Examples of lower alkyl fragments include methyl, ethyl, propyl, isopropyl, butyl sec- and tert-butyl, pentyl hexyl, heptyl, cyclopropyl, cyclobutyl, cyclopentyl, cyclohexyl, cycloheptyl, 1-propenyl, 2-butenyl, 2-methyl-2-butenyl, 2-butynyl and the like.

As used herein, the term alkyl means lower alkyl and extends to cover carbon fragments having up to 20 carbon atoms in straight, branched or cyclic configurations. Moreover, alkyl means carbon fragments having one or more double or triple bonds, conjugated or unconjugated. Examples of alkyl groups include octyl, nonyl, undecyl, dodecyl, tridecyl, tetradecyl, pentadecyl, eicosyl, 3,7-ethyl-2,2-methyl-4-propylnonane and the like.

As used herein, the term aryl means the carbon containing aromatic structures phenyl, naphthyl, anthracenyl, phenanthrenyl, pyrenyl, phenyl substituted with one or more alkyls, naphthyl substituted with one or more alkyls, anthracenyl substituted with one or more alkyls, phenanthrenyl substituted with one as more alkyl.

As used herein, heterocyclic rings include 5 or 6 membered rings containing one or more heteroatoms selected from O, N, S and bicyclic fused rings containing one or more heteroatoms selected from O, N or S. Generally useful heterocyclic rings (where the the broken lines indicate optional double bonds) include:

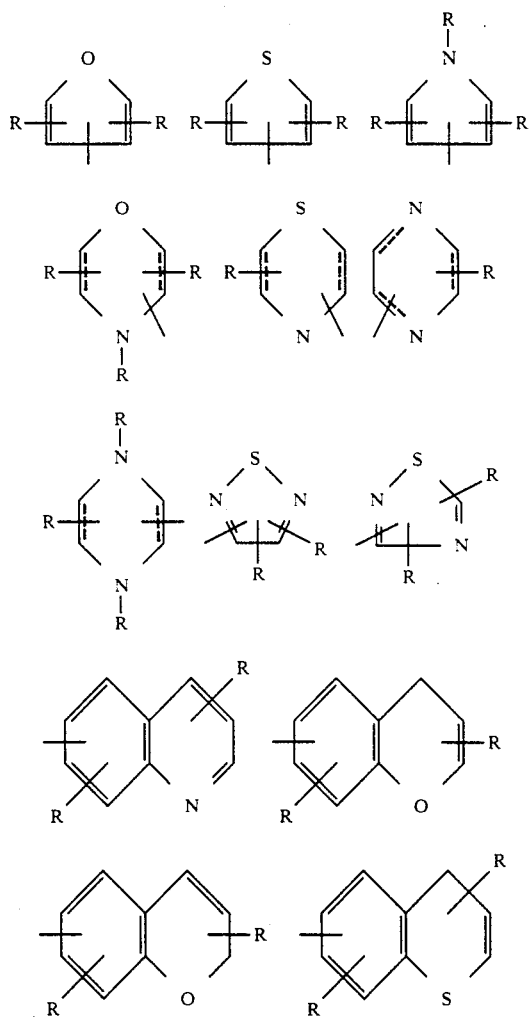

and the like, wherein R is any of R$^1$, R$^2$, R$^3$, R$^4$, R$^5$, R$^6$, R$^8$ or R$^9$.

As used herein, the term halogen refers to F, Cl, Br and I.

As used herein, the N-terminally bound essential amino acids are defined as follows: L-alanine, L-valine, L-leucine, L-isoleucine, L-proline, L-phenylalanine, L-tryptophan, L-methionine, L-glycine, L-serine, L-threonine, L-cycteine, L-tyrosine, L-asparagine, L-glutamine, L-lysine, L-arginine, L-histidine, aspartic acid and glutamic acid. The enantiomeric D-amino acids may also be used as N-terminally bonded essential amino acids.

A preferred group of compounds is represented by Formula II:

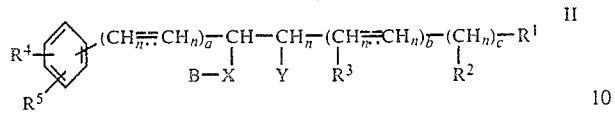

wherein:

n is 0-2 as required to maintain four bonds to carbon;

the broken lines represent optional double or triple bonds;

b and c are each independently 0-5; and $R^2$ and $R^3$ are each independently H, lower alkyl or one $R^2$ and one $R^3$ may be connected by a 1C or 2C bridge to form a cyclic ring which may have 0, 1, 2 or 3 double bonds;

$R^1$ is $COOR^2$, $CH_2OH$, CHO, tetrazole, hydroxymethyl ketone, CN, $CONR^2R^4$, a monocyclic or bicyclic heterocyclic ring containing an acidic hydroxyl group or $NHSO_2R^4$; or

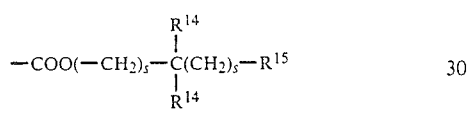

wherein each s is independently 0-3; each $R^{14}$ is independently H or alkyl of 1 to 4 carbons which may be straight chain or branched; $R^{15}$ is (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or (B) the radical $X-R^{16}$ wherein X is O, S or NH and $R^{16}$ contains up to 21 carbon atoms which may be straight chain or branched and is (1) a hydrocarbon radical or (2) an acyl radical of an organic acyclic or monocyclic carboxylic acid containing not more than 1 heteroatom selected from N, O or S in the ring:

$R^4$ is H; alkyl; hydroxyl; halogen; haloalkyl; benzyl; benzyl substituted with at least one $R^7$; aryl; aryl substituted with at least one $R^5$; $NO_2$; CN; $SCF_3$; $OR^5$; O-benzyl; O-benzyl substituted with at least one $R^5$; O-aryl; O-aryl substituted with at least one $R^5$; $SR^5$; $NR^2R^5$; $SOR^5$ or $SO_2R^5$;

$R^5$ is H; alkyl; hydroxyl; halogen; haloalkyl; benzyl; benzyl substituted with at least one $R^3$; $NO_2$; CN; $SCF_3$; $OR^3$; O-benzyl; O-benzyl substituted with at least one $R^3$; O-aryl; O-aryl substituted with at least one $R^3$; $SR^3$; $NR^2R^3$; $SOR^3$ or $SO_2R^3$;

$R^7$ is H, alkylthioalkyl, alkylthiobenzyl or alkylthioaryl;

Y is H or OH;

X is O or S;

B is H,

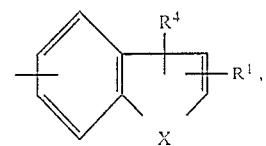

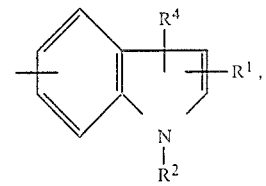

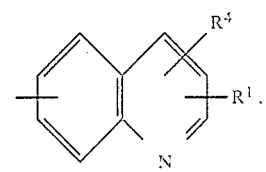

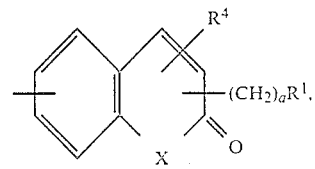

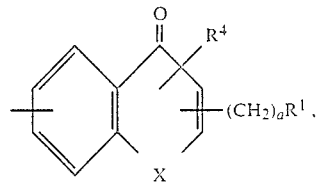

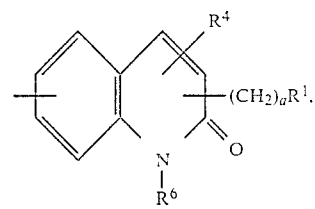

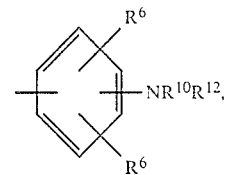

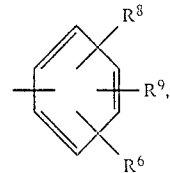

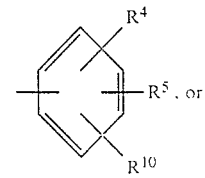

-continued

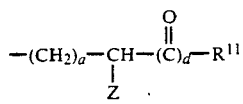

wherein

Z is H, NHR$^9$, NR$^2$R$^9$, an N-terminal bonded essential amino acid or a lower alkyl ester thereof, OH, OR$^4$ or OR$^2$;

each R$^6$ is H, lower alkyl, halogen, OR$^2$, SR$^2$, SOR$^4$ or SO$_2$R$^5$;

R$^8$ is H, lower alkyl or —(CH$_2$)$_a$R$^1$;

R$^9$ is H,

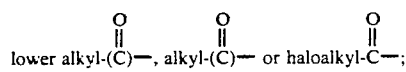

R$^{10}$ is

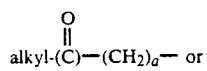

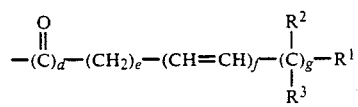

wherein e is 0 to 9 and f and g are independently 0 to 3;

R$^{11}$ is Z, wherein Z is as defined above, when d is 1 and R$^{11}$ is R$^1$ or Z, wherein Z is as defined above, when d is 0;

R$^{12}$ is as defined for Formula I;

each a in the above definitions is independently 0 or 1 and each d in the above definitions is independently 0 or 1.

More preferred are the compounds of Formula II wherein B is selected from:

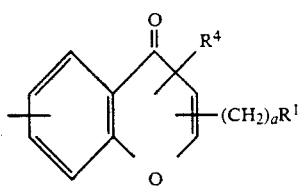

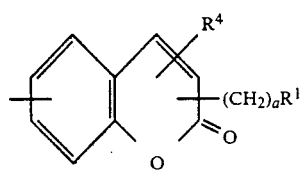

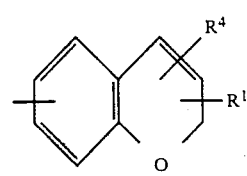

-continued

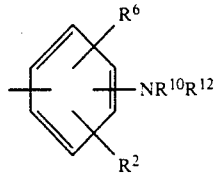

wherein the substituents are as defined above.

Pharmaceutically acceptable salts of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, tri-methylamine, diethanolamine, diethylamine, triethylamine, tripropylamine, ethanolamine, 2-dimethylaminoethanol, 2-diethylaminoethanol, tomethamine, lysine, arginine, histidine, caffeine, procaine, hydrabamine, choline, imidazole, betaine, ethylenediamine, glucosamine, methylglucamine, theobromine, purines, piperazine, N,N'-dibenzylethylenediamine, piperidine, N-ethyl-piperidine, morpholine, N-ethylmorpholine, polyamine resins and the like.

As indicated above, the compound of Formula I are active as antagonists of SRS-A and the leukotrienes B$_4$, C$_4$, D$_4$ and E$_4$. This activity can be detected and evaluated by methods known in the art. See for example, Kadin, U.S. Pat. No. 4,296,129.

The ability of the compounds of Formula I to antagonize the effects of the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma.

A compound of Formula I, or a pharmaceutically acceptable salt thereof, can be administered to a human subject either alone, or preferably, in combination with pharmaceutically acceptable carriers or diluents, in a pharmaceutical composition, according to standard pharmaceutical practice. A compound can be administered orally or parenterally. Parenteral administration includes intravenous, intramuscular, intraperitoneal, subcutaneous and topical administration, and also administration by inhalation and insufflation.

For oral use of an leukotriene antagonist of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic. For administration by inhalation or insufflation, it is convenient to prepare an aqueous or partially aqueous solution of a compound of Formula I or salt thereof, and then this solution is administered in form of an aerosol.

When a compound of Formula I or salt thereof is used as an leukotriene antagonist in a human subject, the daily dosage will normally be determined by the prescribing physician. Moreover, the dosage will vary according to the age, weight and response of the individual patient, as well as the severity of the patient's symptoms. However, in most instances, and effective daily dosage will be in the range from about 0.1 to about 40 mg per kg, and preferably 0.2 to 20 mg per kg, most preferably 1 to 10 mg per kg in a single or divided doses. On the other hand, it may be necessary to use dosages outside these limits in some cases.

In addition to the compounds of Formula I, pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

NSAIDS can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprufen, ketoprufen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

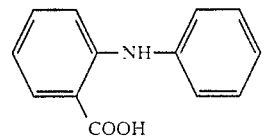

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

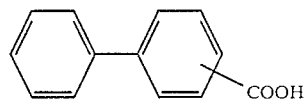

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

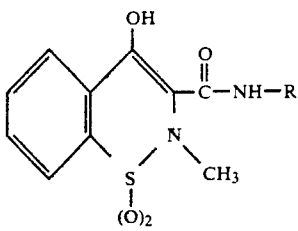

wherein R is an aryl or heteroaryl ring system.

The following NSAIDS may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones and pharmaceutically acceptable salts thereof.

The compounds of the Formula I may also be used in combination with leukotriene antagonists known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as a-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP No. 40,696 and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

PREPARATION OF COMPOUNDS—GENERAL DESCRIPTION

The compounds of Formula I may be prepared by any process available to the skilled artisan. General reaction schemes are as follows:

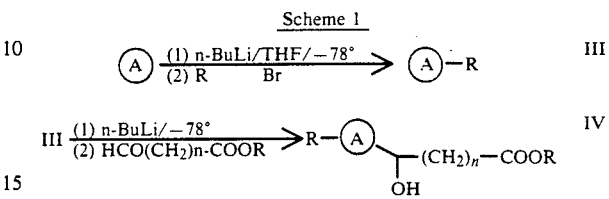

As described in Scheme 1, heteroaromatics A such as thiophene, furan and the like, may be reacted with a strong base, such as n-butyllithium. The resulting lithiated compound may then be reacted with an alkyl or alkenyl halide compound to produce the compound III.

Compound III may be reacted with a strong base, such as n-butyllithium, and the resulting lithiated species may be reacted with an omega-formyl alkanoic acid ester to yield a compound of Formula IV.

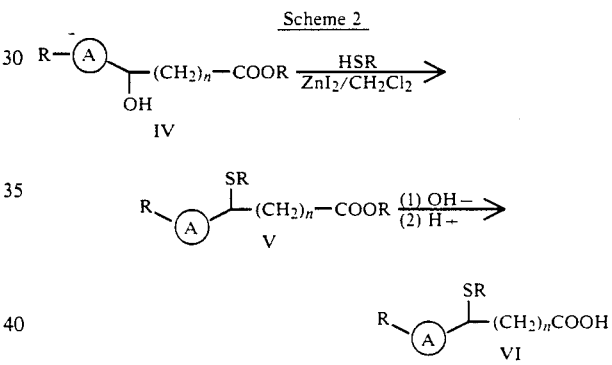

Compounds of Formula IV (all aromatics) may be reacted with a thiol in the presence of a Lewis Acid such as zinc iodide to yield the thiol compound of Formula V (Scheme 2).

Compound V may be hydrolyzed by conventional means to yield the free acid compound of Formula VI.

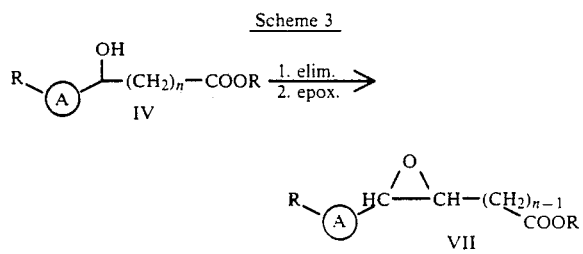

Compounds of Formula IV may be treated with a catalytic amount of a strong acid, for example, p-toluenesulfonic acid, to eliminate water, thus forming an olefin. This olefin may then be reacted with an epoxidizing agent, such as m-chloroperbenzoic acid, to provide an epoxide compound of Formula VII (Scheme 3).

Scheme 4

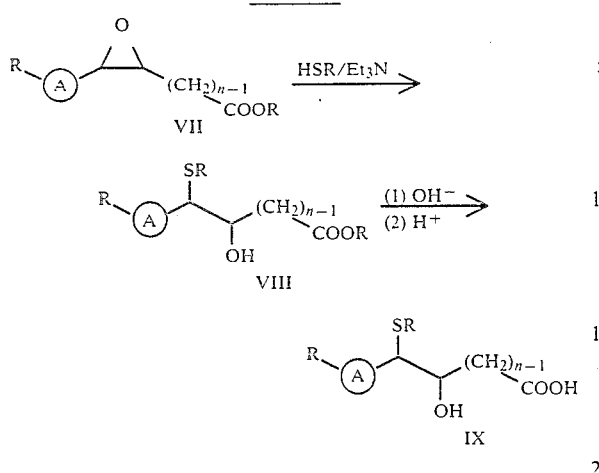

As shown in Scheme 4, the epoxide compounds of Formula VII may be reacted with a thiol compound in the presence of a base such as triethylamine, sodium hydride, and the like, to yield a β-hydroxy sulfide compound of the Formula VIII. The β-hydroxy sulfide compound VIII may be hydrolyzed by conventional means to provide the free acid compound of Formula IX.

Scheme 5

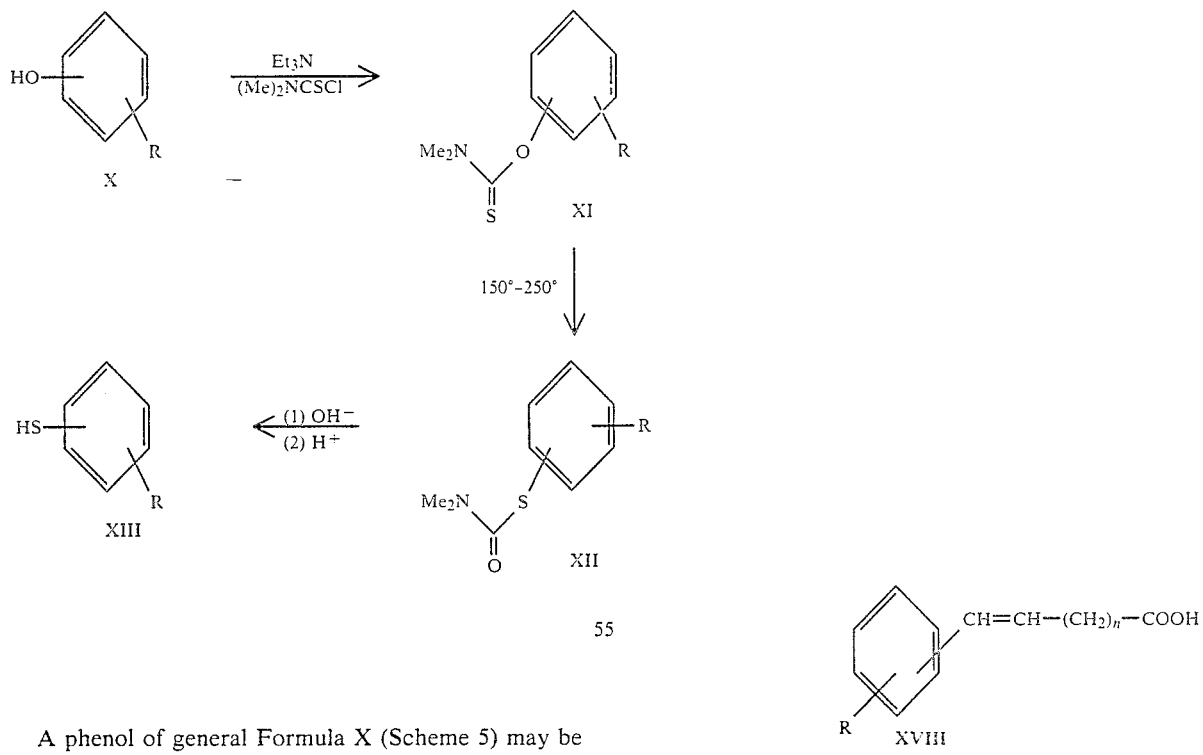

A phenol of general Formula X (Scheme 5) may be reacted with dimethyl thiocarbamylchloride in the presence of a base such as triethylamine, sodium hydride and the like to yield the compound having general Formula XI. Compound XI may be heated at from 150° to 250° C. either neat or in a suitable solvent, to provide the compound of Formula XII. Compound XII may be reacted with a base such as an alkoxide or hydroxide, and followed by acidification, generates the thiol compound having the Formula XIII.

Scheme 6

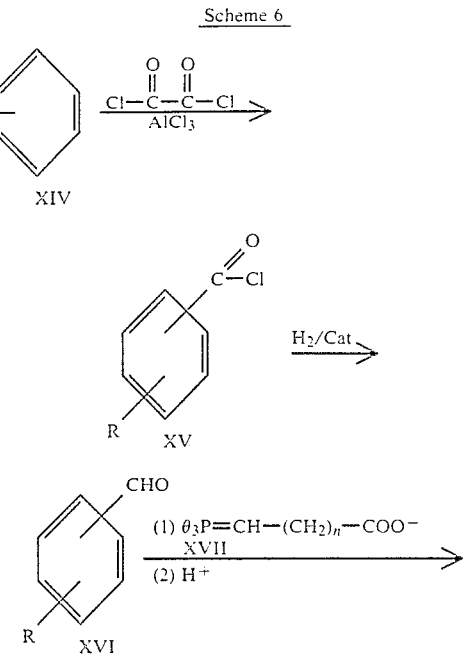

Substituted aromatic compounds having the general Formula XIV (Scheme 6) may be reacted with oxalyl chloride in the presence of a Lewis Acid. such as aluminum chloride, to provide the acid chloride compound of Formula XV. The acid chloride may be reduced by conventional means, for example by catalytic hydrogenation, to provide the aldehyde of general Formula XVI. Aldehyde XVI may be reacted with a Wittig reagent of general Formula XVII to yield, following acidification, the olefin compound of Formula XVIII.

Scheme 7

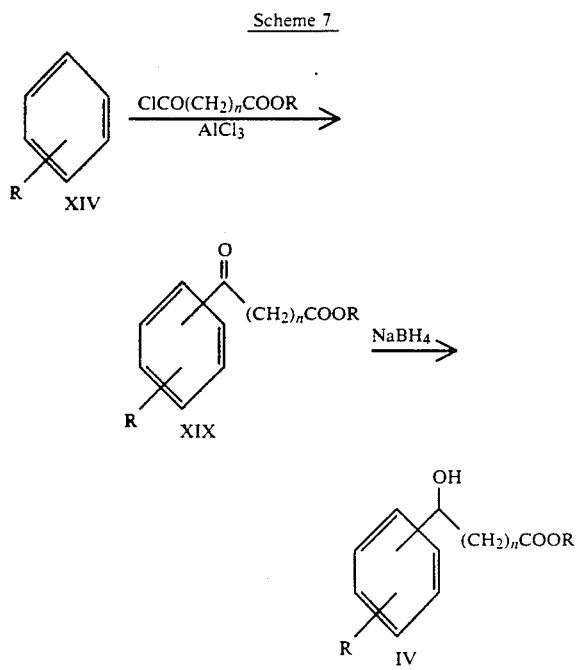

Substituted aromatic compounds of general Formula XIV may be reacted with an omega chloroformyl alkanoic acid ester or cyclic anhydride in the presence of a Lewis Acid, such as aluminum chloride to provide the ketone of general Formula XIX (Scheme 7).

Ketone XIX may be reduced using conventional techniques, for example, sodium borohydride, to provide the alcohol of general Formula IV.

Scheme 8

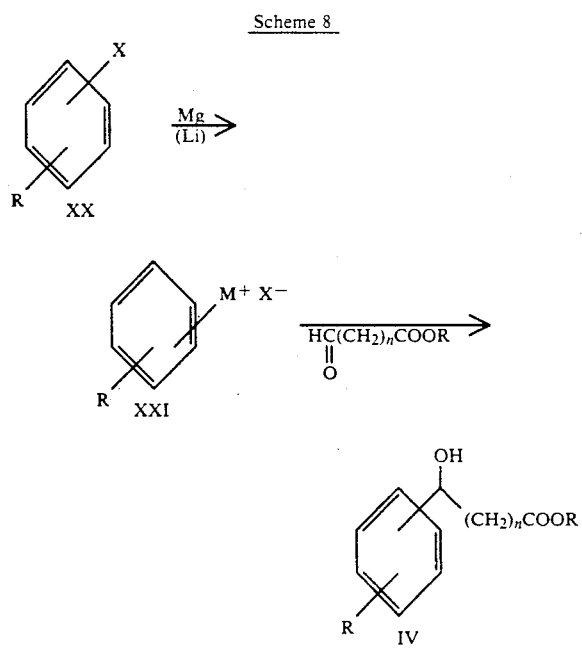

Halogen (Cl, Br, I) substituted aromatic compounds of general Formula XX may be reacted with magnesium or lithium to generate the metalated species XXI. The metalated species may be reacted with an omega-formyl alkanoic acid ester to provide the alcohol of general Formula IV (Scheme 8).

Scheme 9

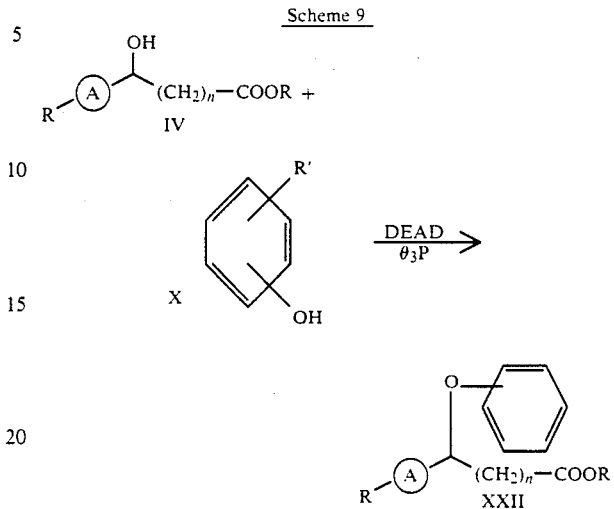

As shown in Scheme 9, an alcohol of general Formula IV may be reacted with a phenol of genera Formula X in the presence of a molar equivalent amount of diethylazodicarboxylate (DEAD) and triphenylphosphine to provide the ether compound of general Formula XXII.

Pro-drug esters wherein $R^1$ is a monocyclic or bicyclic heterocyclic ring containing an acidic hydroxyl group are obtained by reacting the appropriate heterocycle with a compound of Formula I ($R^1$=COOH) in the presence of dicyclohexylcarbodiimide and hydroxybenzotriazole in an inert solvent such as DMF.

Pro-drug esters wherein $R^1$ is

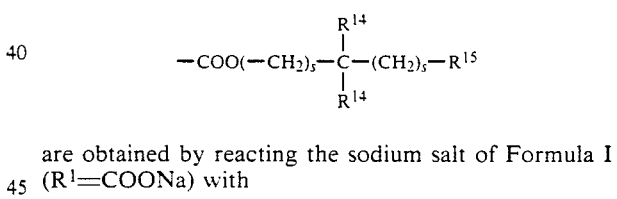

are obtained by reacting the sodium salt of Formula I ($R^1$=COONa) with

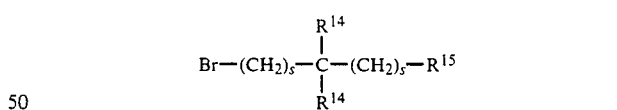

in an inert solvent such as DMF.

Examples 1 through 125 of U.S. Pat. No. 4,609,744 (Young et al.) are incorporated herein by reference.

What is claimed is:

1. A compound which is:
   (±)-Erythro-2-methoxy-7-((5-carboxy-2-hydroxy-1-(4-nonylphenyl)pentyl)thio)-3-quinoline-carboxylic acid;
   (±)-erythro-2-butoxy-7((5-carboxy-2-hydroxy-1-(4-nonylphenyl)pentyl)thio)-3-quinoline-carboxylic acid;
   D,L-erythro-7-((5-carboxy-1-(1,2-dihydro-5-acenaphthalenyl)-2-hydroxypentyl)thio)-2-methoxy-3-quinoline-carboxylic acid disodium salt trihydrate;
   D,L-erythro-7-((5-carboxy-2-hydroxy-1-(4-(2-phenylethyl)phenyl)pentyl)thio)-2-methoxy-3-quinoline-carboxylic acid disodium salt dihydrate; or D.L-erythro-7-((5-carboxy-2-hydroxy-1-(5,6,7,8-tetrahydro-2-naphthalenyl)pentyl)thio)-2-methoxy-3-quinoline-carboxylic acid disodium salt sesquihydrate.

2. A pharmaceutical composition effective as a leukotriene antagonist, containing a pharmaceutically effective amount of a compound of claim 1 and a pharmaceutically acceptable carrier.

* * * * *